United States Patent
Li et al.

(10) Patent No.: US 10,183,903 B2
(45) Date of Patent: Jan. 22, 2019

(54) METHOD FOR PREPARING 2,3,3,3-TETRAFLUOROPROPENE USING METHYL MAGNESIUM CHLORIDE

(71) Applicant: JUHUA GROUP TECHNOLOGY CENTER, Quzhou, Zhejiang Province (CN)

(72) Inventors: Hongfeng Li, Quzhou (CN); Shuhua Wang, Quzhou (CN); Xiaobo Xu, Quzhou (CN); Liyong Ma, Quzhou (CN)

(73) Assignee: JUHUA GROUP TECHNOLOGY CENTER, Quzhou (CN)

( * ) Notice: Subject to any disclaimer, the term of this patent is extended or adjusted under 35 U.S.C. 154(b) by 0 days.

(21) Appl. No.: 15/551,580

(22) PCT Filed: Dec. 24, 2015

(86) PCT No.: PCT/CN2015/098537
§ 371 (c)(1),
(2) Date: Aug. 16, 2017

(87) PCT Pub. No.: WO2017/028442
PCT Pub. Date: Feb. 23, 2017

(65) Prior Publication Data
US 2018/0029961 A1    Feb. 1, 2018

(30) Foreign Application Priority Data
Aug. 18, 2015 (CN) .......................... 2015 1 0508207

(51) Int. Cl.
| | | |
|---|---|---|
| C07C 17/263 | (2006.01) | |
| C07C 17/02 | (2006.01) | |
| C07C 17/04 | (2006.01) | |
| C07C 21/18 | (2006.01) | |
| C07C 17/25 | (2006.01) | |

(52) U.S. Cl.
CPC .......... *C07C 17/2632* (2013.01); *C07C 17/02* (2013.01); *C07C 17/04* (2013.01); *C07C 17/25* (2013.01); *C07C 21/18* (2013.01)

(58) Field of Classification Search
CPC ................................ C07C 17/02; C07C 17/04
See application file for complete search history.

(56) References Cited

U.S. PATENT DOCUMENTS

2011/0270000 A1* 11/2011 Bektesevic ........... C07C 17/087
570/156
2012/0330072 A1* 12/2012 Nagai .................... B01J 23/892
570/144

FOREIGN PATENT DOCUMENTS

| CN | 101213162 A | 7/2008 |
| CN | 103958553 A | 7/2014 |
| CN | 105111038 A | 12/2015 |
| WO | WO2007123786 A1 | 11/2007 |

OTHER PUBLICATIONS

Rozen, S. et al. "Direct Addition of Elemental Fluorine to Double Bonds" J. Org. Chem., vol. 51, No. 19, 1986, pp. 3607-3611 (Year: 1986).*

* cited by examiner

Primary Examiner — Medhanit W Bahta
(74) Attorney, Agent, or Firm — Jiwen Chen

(57) ABSTRACT

The present invention discloses a method for preparing 2,3,3,3-tetrafluoropropene using methylmagnesium chloride, comprising the following steps: 1) preparing 1,1,2-trifluoropropene ($CH_3CF=CF_2$); 2) preparing 1,1,1,2,2-pentafluoropane ($CF_3CF_2CH_3$); 3) preparing 2,3,3,3-tetrafluoropropene ($CF_3CF=CH_2$). In the present invention, using a Grignard reagent, namely methylmagnesium chloride, and tetrafluoroethylene as starting raw materials, 2,3,3,3-tetrafluoropropene is prepared by three steps of nucleophilic addition-elimination, fluorine addition, and dehydrofluorination in sequence. The process flow is relatively short, and the product yield is high.

5 Claims, No Drawings

METHOD FOR PREPARING 2,3,3,3-TETRAFLUOROPROPENE USING METHYL MAGNESIUM CHLORIDE

This is a U.S. national stage application of PCT Application No. PCT/CN2015/098537 under 35 U.S.C. 371, filed Dec. 24, 2015 in Chinese, claiming the priority of Chinese Patent Application No. 201510508207.4 filed Aug. 18, 2015, which is hereby incorporated by reference.

BACKGROUND OF THE INVENTION

1. Technical Field

The present invention relates to a method for preparing 2,3,3,3-tetrafluoropropene, in particular to a method for preparing 2,3,3,3-tetrafluoropropene by using methylmagnesium chloride and tetrafluoroethylene as starting raw materials by three steps of nucleophilic addition and elimination, fluorine addition, and dehydrofluorination.

2. Description of Related Art 2,3,3,3-tetrafluoropropene, with a molecular formula of $CF_3CF=CH_2$, a boiling point of $-28.3°$ C., a CAS No. of 754-12-1, 0 ODP and 4 GWP, has good weather fastness during the life time, but only has 11 days of atmosphere life time. Such material has excellent physical and chemical properties, has a molecular weight similar to that of HFC-134a, a relatively low boiling point, a relatively high saturated vapor pressure at room temperature, and a density and a clinical point similar to those of HFC-134a, and therefore is deemed as a "direct substitute" for HFC-134a. 2,3,3,3-tetrafluoropropene has become one of the most potential fourth-generation low-carbon refrigerants.

In accordance with the literature and existing patents, at present, the synthesis methods of the 2,3,3,3-tetrafluoropropene mainly include the tetrafluoroethylene method, trifluoropropyne method, trifluoropropene method, tetrafluoropropanol method, hexafluoropropylene (HFP) method, tetrachloropropene method, HCFC-242 method, difluorochloromethane method, $CF_3COCH_2COCF_3$ method, HFO-1234ze isomerization method, etc. in terms of starting raw materials. Among the methods, the hexafluoropropylene (HFP) method is one of the hottest research points. For example, patents US20070179324A, CN102267869A and CN102026947A disclose using hexafluoropropylene as the starting raw material to prepare $CF_3CF=CH_2$ by four reaction steps of hydrogenation, dehydrofluorination, hydrogenation and dehydrofluorination. Even so, the methods provided by such patents still have disadvantages such as numerous and complicated steps, large equipment investment, high separation cost, large energy consumption, high emission of waste gases, liquids and solids.

The patent CN103708988A discloses a synthesis method which uses polytrifluorostyrene compounds. According to such method, halogenated benzene and magnesium perform a Grignard reaction in an organic solvent to generate a Grignard reagent, and then the Grignard and tetrafluoroethylene react to synthesize the polytrifluorostyrene.

BRIEF SUMMARY OF THE INVENTION

Aiming at the defects in prior art, the present invention provides a technical solution of a method for synthesizing 2,3,3,3-tetrafluoropropene by using methylmagnesium chloride and tetrafluoroethylene as starting raw materials. Using a Grignard reagent, namely methylmagnesium chloride, and tetrafluoroethylene as the starting raw materials, 2,3,3,3-tetrafluoropropene is prepared by three steps of nucleophilic addition, elimination and fluorine addition in sequence, and dehydrofluorination. The process flow is relatively short, and the product yield is high.

To solve the above technical problems, the present invention employs the following technical solution:

A method for preparing 2,3,3,3-tetrafluoropropene by using methylmagnesium chloride is characterized by comprising the following steps:

1) Preparing 1,1,2-trifluoropropene ($CH_3CF=CF_2$)
wherein tetrafluoroethylene and the Grignard reagent, namely methylmagnesium chloride, react in a first organic solvent to obtain 1,1,2-trifluoropropene, wherein the molar ratio of methylmagnesium chloride to tetrafluoroethylene is 1:1-1:5, the reaction temperature is from $-20°$ C. to $40°$ C., the main side product is $CH_3$—$CF=CF$—$CF_2$—$CF_2$—$CH_3$;

2) Preparing 1,1,1,2,2-pentafluoropane ($CF_3CF_2CH_3$)
wherein at a temperature of $-30°$ C., a second organic solvent and the 1,1,2-trifluoropropene obtained in step 1) are added into a reactor with a stirrer; the reaction temperature is controlled; then, the mixture of fluorine and nitrogen gases is continuously input into the reactor, and a reaction proceeds, wherein the mass ratio of 1,1,2-trifluoropropene to solvent is 1:0.5-1:5, the molar ratio of 1,1,2-trifluoropropene to fluorine gas is 1:1-1:1.2; when the amount of the input fluorine gas reaches a predetermined value, the reaction is stopped; the residual fluorine gas is blown using the nitrogen gas; the reaction liquid is rectified, and then 1,1,1,2,2-pentafluoropane is obtained;

3) preparing 2,3,3,3-tetrafluoropropene ($CF_3CF=CH_2$)
wherein the 1,1,1,2,2-pentafluoropane obtained in step 2) is input into the reactor containing an alkaline solution; then a reaction proceeds; a gas product is dried and compressed to obtain the product 2,3,3,3-tetrafluoropropene, wherein the concentration of the alkaline solution is 10-50%, and the reaction temperature is 50-90° C.

Further, the first organic solvent in step 1) is any one of tetrahydrofuran, diethyl ether and glycol dimethyl ether, which can effectively enhance the reaction degree of the tetrafluoroethylene and the Grignard reagent, namely methylmagnesium chloride, and the organic solvent serves as a catalyst, promoting smooth reaction.

Further, the second organic solvent in step 2) is any one of 1,1,2-trichlorotrifluoroethane, perfluoro-n-butane, perfluorohexane and perfluorooctane which are fully halogenated solvents, ensuring that the reaction in step 2) proceeds in a tender state.

Further, the mixture of fluorine and nitrogen gases in step 2) contains 5-30% of fluorine gas, ensuring that the reaction in step 2) proceeds in a tender state, and improving safety.

Further, the alkaline solution in step 3) is potassium hydroxide, sodium hydroxide or a mixture thereof.

In the present invention, $CH_3MgCl$ and $CF_2=CF_2$ react to synthesize $CH_3CF_2CF_2MgCl$, but $CH_3CF_2CF_2MgCl$ itself is unstable and quickly performs the elimination reaction to generate $CH_3CF=CF_2$; then, $CH_3CF=CF_2$ and $F_2/N_2$ react at a low-temperature solvent to generate $CH_3CF_2CF_3$; and finally, $CH_3CF_2CF_3$ is removed from HF using the alkaline solution to synthesize and obtain $CF_3CF=CH_2$. The reaction path is as follows.

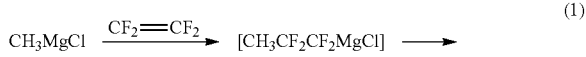

(1)

-continued

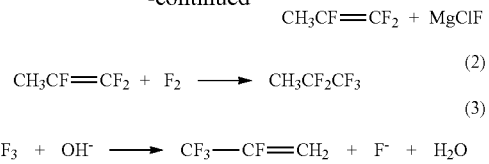

The present invention employing the above technical solution has the following beneficial effects:

The 2,3,3,3-tetrafluoropropene is prepared by using methylmagnesium chloride, namely the Grignard reagent, and tetrafluoroethylene as the starting raw materials by three steps of nucleophilic addition, elimination and fluorine addition, and dehydrofluorination. The process flow is relatively short, and the product yield is high.

DETAILED DESCRIPTION OF THE INVENTION

The present invention provides a method for preparing 2,3,3,3-tetrafluoropropene by using methylmagnesium chloride, comprising the following steps:

1) preparing 1,1,2-trifluoropropene ($CH_3CF$=$CF_2$)

wherein tetrafluoroethylene and the Grignard reagent, namely methylmagnesium chloride, react in an organic solvent to obtain 1,1,2-trifluoropropene, wherein the organic solvent is any one of tetrahydrofuran, diethyl ether and glycol dimethyl ether, which can effectively enhance the reaction degree of the tetrafluoroethylene and the Grignard reagent, and the organic solvent serves as a catalyst, promoting smooth reaction, the molar ratio of methylmagnesium chloride to tetrafluoroethylene is 1:1-1:5, the reaction temperature is −20-40° C.; the reaction pressure is 1-3 Mpa, the main side product is $CH_3$—$CF$=$CF$—$CF_2$—$CF_2$—$CH_3$;

2) preparing 1,1,1,2,2-pentafluoropane ($CF_3CF_2CH_3$)

wherein at a temperature of −30° C., the solvent and 1,1,2-trifluoropropene obtained in step 1) are added into a reactor with a stirrer, wherein the solvent is any one of 1,1,2-trichlorotrifluoroethane, perfluoro-n-butane, perfluorohexane and perfluorooctane which are fully halogenated solvents, ensuring that the reaction in step 2) proceeds in a tender state; the reaction temperature is controlled; then, the mixture of fluorine and nitrogen gases is continuously input into the reactor, and a reaction proceeds, wherein the mixture of fluorine and nitrogen gases contains 5-30% of fluorine gas, ensuring that the reaction in step 2) proceeds in a tender state, and improving safety, the mass ratio of 1,1,2-trifluoropropene to solvent is 1:0.5-1:5, the molar ratio of 1,1,2-trifluoropropene to fluorine gas is 1:1-1:1.2; when the amount of the input fluorine gas reaches a predetermined value, the reaction is stopped; the residual fluorine gas is blown using the nitrogen gas; the reaction liquid is rectified, and then the 1,1,1,2,2-pentafluoropane is obtained;

3) preparing 2,3,3,3-tetrafluoropropene ($CF_3CF$=$CH_2$)

wherein the 1,1,1,2,2-pentafluoropane obtained in step 2) is input into the reactor containing an alkaline solution, and then a reaction proceeds, wherein the alkaline solution is potassium hydroxide, sodium hydroxide or a mixture thereof; a gas product is dried and compressed to obtain the product 2,3,3,3-tetrafluoropropene, wherein the concentration of the alkaline solution is 10-50%, and the reaction temperature is 50-90° C.

In the present invention, $CH_3MgCl$ and $CF_2$=$CF_2$ react to synthesize $CH_3CF_2CF_2MgCl$, but $CH_3CF_2CF_2MgCl$ itself is unstable and quickly performs the elimination reaction to generate $CH_3CF$=$CF_2$; then, $CH_3CF$=$CF_2$ and $F_2/N_2$ react at a low-temperature solvent to generate $CH_3CF_2CF_3$; and finally, $CH_3CF_2CF_3$ is removed from HF using the alkaline solution to synthesize and obtain $CF_3CF$=$CH_2$. The reaction path is as follows.

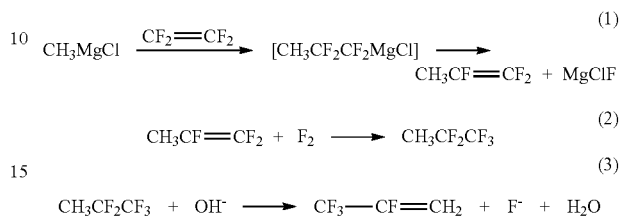

Embodiment 1

1) Preparation of 1,1,2-trifluoropropene

A 2 L stainless steel high-pressure reactor was filled with the nitrogen gas three times to exchange the air therein; then 250 g (2 mol/Kg) of methylmagnesium chloride, namely the Grignard reagent, and 750 g of tetrahydrofuran were added into the reactor; the mixed materials were stirred while cooled; at the temperature of −13° C., 120 g of tetrafluoroethylene was input with stirring. After the tetrafluoroethylene was added, the mixed materials were slowly heated until the temperature in the container rose to 40° C., and the reaction proceeded for 5 h at the temperature of 40° C. When the reaction ended, heating was stopped and the materials were stirred. The residual tetrafluoroethylene is drained and then the materials were discharged. Then, the 1,1,2-trifluoropropene synthesizing liquid was obtained at a yield of 90.3%. After rectification and purification, the purity of the obtained product was 99.5%.

2) Preparation of 1,1,1,2,2-pentafluoropropane

An identical 2 L stainless steel high-pressure reactor was degreased and passivated with the fluorine gas, and then added with 1,000 g of the solvent, 1,1,2-trichlorotrifluoroethane, 500 g (5.21 mol) of 1,1,2-trifluoropropene; the reactor was continuously cooled until the temperature reached −60° C., and 15% mixture of the fluorine and nitrogen gases was continuously input into the reactor within 2 h by using a flowmeter. When the amount of the input fluorine gas reached 5.47 mol, the reaction was stopped, and the residual fluorine gas was blown with the nitrogen gas. The reaction yield was 92%. After rectification, the 1,1,1,2,2-pentafluoropropane with a purity of 99.5% was obtained.

3) Preparation of 2,3,3,3-tetrafluoropropene

The 1,1,1,2,2-pentafluoropropane obtained in step 2 passed through 40% potassium hydroxide solution at a temperature of 70° C.; the reaction product was dried, condensed and collected, and then the 2,3,3,3-tetrafluoropropene product with a purity of 99.5% was obtained at a yield of 98.2%.

The total yield of the three reaction steps was 81.6%.

Embodiment 2

1) Preparation of 1,1,2-trifluoropropene

The materials used in step 1 of embodiment 1 were replaced by 250 g (2 mol/Kg) of methylmagnesium chloride, 750 g of tetrahydrofuran and 250 g of tetrafluoroethylene.

Other conditions were identical with the corresponding conditions in step 1 of embodiment 1. The 1,1,2-trifluoropropene synthesizing liquid was obtained at a yield of 93.6%.

2) Preparation of 1,1,1,2,2-pentafluoropropane

The materials used in step 2 of embodiment 1 were replaced by 1,000 g of solvent, namely 1,1,2-trichlorotrifluoroethane, 500 g (5.21 mol) of 1,1,2-trifluoropropene, and 5% mixture of fluorine and nitrogen gases that has a total fluorine gas content of 6.25 mol. Other conditions were identical with the corresponding conditions in step 2 of embodiment 1. The reaction yield of the 1,1,1,2,2-pentafluoropane was 95.4%.

3) Preparation of 2,3,3,3-tetrafluoropropene

The concentration of the alkaline solution used in step 3 of embodiment 1 was changed into 60%, and the 2,3,3,3-tetrafluoropropene yield was 99.1%.

The total yield of the three reaction steps was 88.5%.

Embodiment 3

1) Preparation of 1,1,2-trifluoropropene

The temperature of the 1,1,2-trifluoropropene synthesis reaction in step 1 of embodiment 1 was changed into 10° C. Other conditions were identical with the corresponding conditions in step 1 of embodiment 1. The 1,1,2-trifluoropropene synthesizing liquid was obtained at a yield of 86.7%.

2) Preparation of 1,1,1,2,2-pentafluoropropane

The fluorine gas in step 2 of embodiment 1 was changed into 30% mixture of fluorine and nitrogen gases, and the input amount was unchanged. Other conditions were identical with the corresponding conditions in step 2 of embodiment 1. The reaction yield of the 1,1,1,2,2-pentafluoropane was 89.3%.

3) Preparation of 2,3,3,3-tetrafluoropropene

The reaction temperature in step 3 of embodiment 1 was changed into 90° C. Other conditions were identical with the corresponding conditions in step 1 of embodiment 3. The 2,3,3,3-tetrafluoropropene was obtained at a yield of 99.2%.

The total yield of the three reaction steps was 76.8%.

Embodiment 4

The preparation of the 1,1,2-trifluoropropene was identical with the reaction step 1 of embodiment 2. The reaction temperature duration preparation of the 1,1,1,2,2-pentafluoropropane was changed into −30° C., other conditions were identical with the corresponding conditions of embodiment 1, and the yield was 91%. The preparation of 2,3,3,3-tetrafluoropropene was identical with embodiment 1. The total yield of the three reaction steps was 83.6%.

Embodiment 5

The preparation of the 1,1,2-trifluoropropene was identical with the reaction step 1 of embodiment 2. The solvent used to prepare the 1,1,1,2,2-pentafluoropane was changed into 1,200 g perfluorooctane, other conditions were identical with the corresponding conditions of embodiment 1, and the yield was 94.7%. The preparation of 2,3,3,3-tetrafluoropropene was identical with embodiment 1. The total yield of the three reaction steps was 87%.

Embodiment 6

The solvent used in step 2 of embodiment 1 was changed into 1,500 g carbon tetrachloride; the alkaline solution in step 3 was changed into 15% sodium hydroxide solution; step 1 and other conditions were identical with those of embodiment 1. The yields of the 1,1,1,2,2-pentafluoropane and 2,3,3,3-tetrafluoropropene were respectively 87.1% and 94.8%. The total yield of the three reaction steps was 74.6%.

Comparative Example 1

A 2 L stainless steel high-pressure reactor was degreased, passivated with the fluorine gas, cooled to −60° C., and then added with 500 g (5.21 mol) of 1,1,2-trifluoropropene; and 15% mixture of the fluorine and nitrogen gases was continuously input into the reactor within 2 h by using a flowmeter. When the amount of the input fluorine gas reached 5.47 mol, the reaction was stopped, and the residual fluorine gas was blown with the nitrogen gas. The 1,1,1,2,2-pentafluoropane has a selectivity of 81% and a yield of 78%. Other side products include 1,1,1,2,2,3-hexafluoropropane, 1,1,1,2,2,3,3-heptafluoropropane, 1,1,1,1,2,2,3,3,3-octafluoropropane, 1,1,2,3-tetrafluoropropene, 1,1,2,3,3-pentafluoropropene, 1,1,2,3,3,3-hexafluoropropylene, etc.

The above are specific embodiments of the present invention only, but the technical characteristics of the present invention are not limited to the above embodiment. Any simple changes, equivalent substitution or modifications on the basis of the present invention to realize the basically the same technical effects shall be incorporated into the protective scope of the present invention.

The invention claimed is:
1. A method for preparing 2,3,3,3-tetrafluoropropene by using methylmagnesium chloride, characterized by comprising the following steps:
   1) preparing 1,1,2-trifluoropropene ($CH_3CF=CF_2$), wherein tetrafluoroethylene and a Grignard reagent, namely methylmagnesium chloride, react in a first organic solvent to obtain 1,1,2-trifluoropropene, wherein the molar ratio of the methylmagnesium chloride to the tetrafluoroethylene is 1:1-1:5, the reaction temperature is from −20° C. to 40° C.;
   2) preparing 1,1,1,2,2-pentafluoropane ($CF_3CF_2CH_3$) by:
      adding a second organic solvent and the 1,1,2-trifluoropropene obtained in step 1) at a temperature of −30° C. into a reactor with a stirrer, wherein the mass ratio of the 1,1,2-trifluoropropene to the second organic solvent is 1:0.5-1:5;
      controlling the reaction temperature;
      adding continuously a mixture of fluorine and nitrogen gases into the reactor, wherein the molar ratio of the 1,1,2-trifluoropropene to the fluorine gas is 1:1-1:1.2;
      stopping the reaction when the amount of the input fluorine gas reaches a predetermined value;
      blowing the residual fluorine gas with nitrogen gas;
      rectifying the reaction liquid;
      obtaining the 1,1,1,2,2-pentafluoropane;
   3) preparing 2,3,3,3-tetrafluoropropene ($CF_3CF=CH_2$) by:
      adding 1,1,1,2,2-pentafluoropane obtained in step 2) into a reactor containing an alkaline solution, wherein the concentration of the alkaline solution is 10-50%, and the reaction temperature is 50-90° C.;
      drying a gas product to obtain the product 2,3,3,3-tetrafluoropropene.
2. The method for preparing 2,3,3,3-tetrafluoropropene by using methylmagnesium chloride according to claim 1, characterized in that the first organic solvent in step 1) is any one of tetrahydrofuran, diethyl ether and glycol dimethyl ether.

3. The method for preparing 2,3,3,3-tetrafluoropropene by using methylmagnesium chloride according to claim 1, characterized in that the second organic solvent in step 2) is any one of 1,1,2-trichlorotrifluoroethane, perfluoro-n-butane, perfluorohexane and perfluorooctane.

4. The method for preparing 2,3,3,3-tetrafluoropropene by using methylmagnesium chloride according to claim 1, characterized in that the mixture of fluorine and nitrogen gases in step 2) contains 5-30% of fluorine gas.

5. The method for preparing 2,3,3,3-tetrafluoropropene by using methylmagnesium chloride according to claim 1, characterized in that the alkaline solution in step 3) is potassium hydroxide, sodium hydroxide or a mixture thereof.

* * * * *